(12) United States Patent
Rosenberg et al.

(10) Patent No.: US 12,383,707 B2
(45) Date of Patent: *Aug. 12, 2025

(54) ANCHOR INSTRUMENTATION AND METHODS

(71) Applicant: INTERRAD Medical, Inc., Plymouth, MN (US)

(72) Inventors: Michael S. Rosenberg, Eagan, MN (US); Mark R. Christianson, Plymouth, MN (US)

(73) Assignee: INTERRAD Medical, Inc., Plymouth, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/379,736

(22) Filed: Oct. 13, 2023

(65) Prior Publication Data

US 2024/0033485 A1 Feb. 1, 2024

Related U.S. Application Data

(63) Continuation of application No. 17/078,579, filed on Oct. 23, 2020, now Pat. No. 11,813,415, which is a continuation of application No. 16/051,709, filed on Aug. 1, 2018, now Pat. No. 10,814,105, which is a continuation of application No. 15/404,514, filed on Jan. 12, 2017, now Pat. No. 10,058,682, which is a continuation of application No. 14/059,640, filed on Oct. 22, 2013, now Pat. No. 9,545,503, which is a continuation of application No. 13/405,499, filed on Feb. 27, 2012, now Pat. No. 8,585,654, which is a continuation of application No. 12/243,229, filed on Oct. 1, 2008, now Pat. No. 8,147,459.

(60) Provisional application No. 60/978,900, filed on Oct. 10, 2007.

(51) Int. Cl.
*A61M 25/04* (2006.01)
*A61B 17/34* (2006.01)

(52) U.S. Cl.
CPC .......... *A61M 25/04* (2013.01); *A61B 17/3415* (2013.01); *A61B 2017/347* (2013.01); *A61B 2017/3484* (2013.01); *A61B 2017/3488* (2013.01)

(58) Field of Classification Search
CPC ............... A61M 25/04; A61B 17/3415; A61B 2017/347; A61B 2017/3484; A61B 2017/3488
See application file for complete search history.

(56) References Cited

U.S. PATENT DOCUMENTS 2,820,457 A 1/1958 Phillips
5,152,298 A 10/1992 Kreyenhagen et al.
(Continued)

*Primary Examiner* — Dung T Ulsh
*Assistant Examiner* — Nelson Louis Alvarado, Jr.
(74) *Attorney, Agent, or Firm* — Fish & Richardson P.C.

(57) ABSTRACT

Some embodiments of a medical device anchor system include an anchor sleeve that receives a catheter (or other medical instrument) though a working channel of the anchor sleeve. The anchor sleeve may include a first actuator that controls the extension of one or more subcutaneous tines into the subcutaneous region under the skin. The anchor sleeve can also include a second actuator that can cause the anchor sleeve to lock onto an outer portion of the catheter (or other medical instrument) arrange in the working channel.

20 Claims, 5 Drawing Sheets

(56) References Cited

U.S. PATENT DOCUMENTS

| | | | | |
|---|---|---|---|---|
| 5,279,597 | A | * | 1/1994 | Dassa ................ A61M 25/0111 604/165.04 |
| 5,728,133 | A | | 3/1998 | Kontos |
| 6,695,861 | B1 | * | 2/2004 | Rosenberg ............ A61M 25/04 604/174 |
| 8,147,459 | B2 | | 4/2012 | Rosenberg |
| 8,585,654 | B2 | | 11/2013 | Rosenberg et al. |
| 9,545,503 | B2 | | 1/2017 | Rosenberg et al. |
| 10,058,682 | B2 | | 8/2018 | Rosenberg et al. |
| 10,814,105 | B2 | * | 10/2020 | Rosenberg ......... A61B 17/3415 |
| 2007/0078397 | A1 | * | 4/2007 | Weststrate ......... A61B 17/3415 604/164.01 |
| 2014/0046264 | A1 | | 2/2014 | Rosenberg et al. |
| 2017/0120007 | A1 | | 5/2017 | Rosenberg et al. |
| 2018/0339137 | A1 | | 11/2018 | Rosenberg et al. |

* cited by examiner

ANCHOR INSTRUMENTATION AND METHODS

CROSS-REFERENCE TO RELATED APPLICATIONS

This is a continuation of U.S. application Ser. No. 17/078,579, filed on Oct. 23, 2020, which is a continuation of U.S. application Ser. No. 16/051,709, filed on Aug. 1, 2018 (now U.S. Pat. No. 10,814,105), which is a continuation of U.S. application Ser. No. 15/404,514 filed Jan. 12, 2017 (now U.S. Pat. No. 10,058,682), which is a continuation of U.S. application Ser. No. 14/059,640 filed on Oct. 22, 2013 (now U.S. Pat. No. 9,545,503), which is a continuation of U.S. application Ser. No. 13/405,499, filed on Feb. 27, 2012 (now U.S. Pat. No. 8,585,654) by Michael S. Rosenberg et al. and entitled "Anchor Instrumentation And Methods," which is a continuation of U.S. application Ser. No. 12/243,229, filed on Oct. 1, 2008 (now U.S. Pat. No. 8,147,459) by Michael S. Rosenberg et al. and entitled "Anchor Instrumentation And Methods," which claims priority to U.S. Application Ser. No. 60/978,900, filed on Oct. 10, 2007 by Michael S. Rosenberg et al. and entitled "Anchor Instrumentation And Methods," the contents of these earlier applications being fully incorporated herein by reference.

TECHNICAL FIELD

This document relates to anchor instrumentation, such as an anchor device for use in placement of a catheter or other medical instrument.

BACKGROUND

Venous, arterial, and body fluid catheters are commonly used by physicians. For example, such catheters may be used to gain access to the vascular system for dialysis, for introducing pharmaceutical agents, for nutrition or fluids, for hemodynamic monitoring, and for blood draws. Alternatively, catheters can be used for drainage of fluid collections and to treat infection. Following introduction into the patient, the catheter is secured to the patient. In conventional practice, the catheter is commonly secured to the patient using an adhesive tape patch or by suturing an attached hub to the patient's skin.

SUMMARY

Some embodiments of a medical device anchor system include an anchor sleeve that receives a catheter (or other medical instrument) though a working channel of the anchor sleeve. The anchor sleeve may include a first actuator that controls the extension of one or more subcutaneous tines into the subcutaneous region under the skin. The anchor sleeve can also include a second actuator that can cause the anchor sleeve to lock onto the outer body of the catheter (or other medical instrument) arrange in the working channel.

In some embodiments, an anchor sleeve device may include an elongate body that defines at least one working channel extending from a proximal opening to a distal tip opening so as to receive a catheter. The anchor sleeve device may also include a subcutaneous anchor mechanism coupled to the elongate body. The subcutaneous anchor mechanism may have one or more flexible anchors that extend away from the body wall when in a deployed orientation in a subcutaneous layer. The anchor sleeve device may include a first actuator that is adjustable relative to the elongate body so as to shift the flexible anchors to the deployed orientation. The anchor sleeve device may further include a locking device that releasably engages to the catheter when the catheter is received in the working channel. The anchor sleeve device may include a second actuator that is adjustable relative to the elongate body so as to urge the locking device to compress at least a portion of an outer surface of the catheter when the catheter is received in the working channel.

Some embodiments can include a method of delivering a catheter device to an internal body site. The method may include advancing an anchor sleeve through a percutaneous opening so that one or more subcutaneous anchor tines are disposed adjacent to a subcutaneous region. The method may also include advancing a catheter device though a working channel of the anchor sleeve and toward a targeted body site. The catheter device may define at least one lumen that extends to a catheter tip. The method may further include operating a first actuator to deploy the subcutaneous anchor tines into the subcutaneous region. Also, the method may include operating a second actuator to deploy the subcutaneous anchor tines into the subcutaneous region to urge a locking device to compress at least a portion of an outer surface of the catheter when the catheter is received in the working channel.

Some or all of the embodiments described herein may provide one or more of the following advantages. First, some embodiments of the anchor sleeve may include subcutaneous anchors that retain the anchor sleeve in the subcutaneous region. For example, the anchors may comprise adjustable tines comprising a material that exhibits superelasticity when used in a human body (e.g., Nitinol or the like). The anchors can be deployed in the subcutaneous region so as to at least temporarily retain the anchor sleeve in engagement with the patient's body.

Second, some embodiments of the anchor sleeve may include a first actuator device (e.g., a slider device in particular embodiments) that can be actuated to control the extension of the anchors into the subcutaneous region. As such, the anchor tines can be in a retracted position (e.g., retracted into the sleeve body) during passage through the skin surface. Thereafter, the anchor tines can be controllably shifted to the extended position under the skin and in the subcutaneous region so as to anchor the sleeve body to the skin insertion site.

Third, some embodiment of the anchor sleeve may include a second actuator (e.g., a twist device in particular embodiments) that causes the anchor sleeve to releasably lock with the catheter (or other medical instrument) after the catheter has been advanced through the sleeve device toward a targeted location. In some circumstances, the locking device can also form a seal around the catheter when connected thereto. In particular, the locking device may comprise a polymeric seal member (e.g., a silicon cylindrical member or the like) that is compressed upon an outer surface of the catheter device in response to the adjustment of the second actuator.

Fourth, because some embodiments of the anchor sleeve include a first actuator to deploy the anchors and a second actuator to cause the locking engagement, the anchor sleeve can be equipped to isolate these two functions and provide the proper amount of force for each function. For example, the force required to releasably lock the anchor sleeve with the catheter device may be substantially greater than the force required to deploy the anchors in the subcutaneous region. As such, the second actuator can be configured to provide a mechanical advantage for the user so that the locking force is applied in a suitable manner. Also, the first actuator can be configured to deploy the anchors without using an unnecessarily high level of force.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION OF ILLUSTRATIVE EMBODIMENTS

Figure 1:
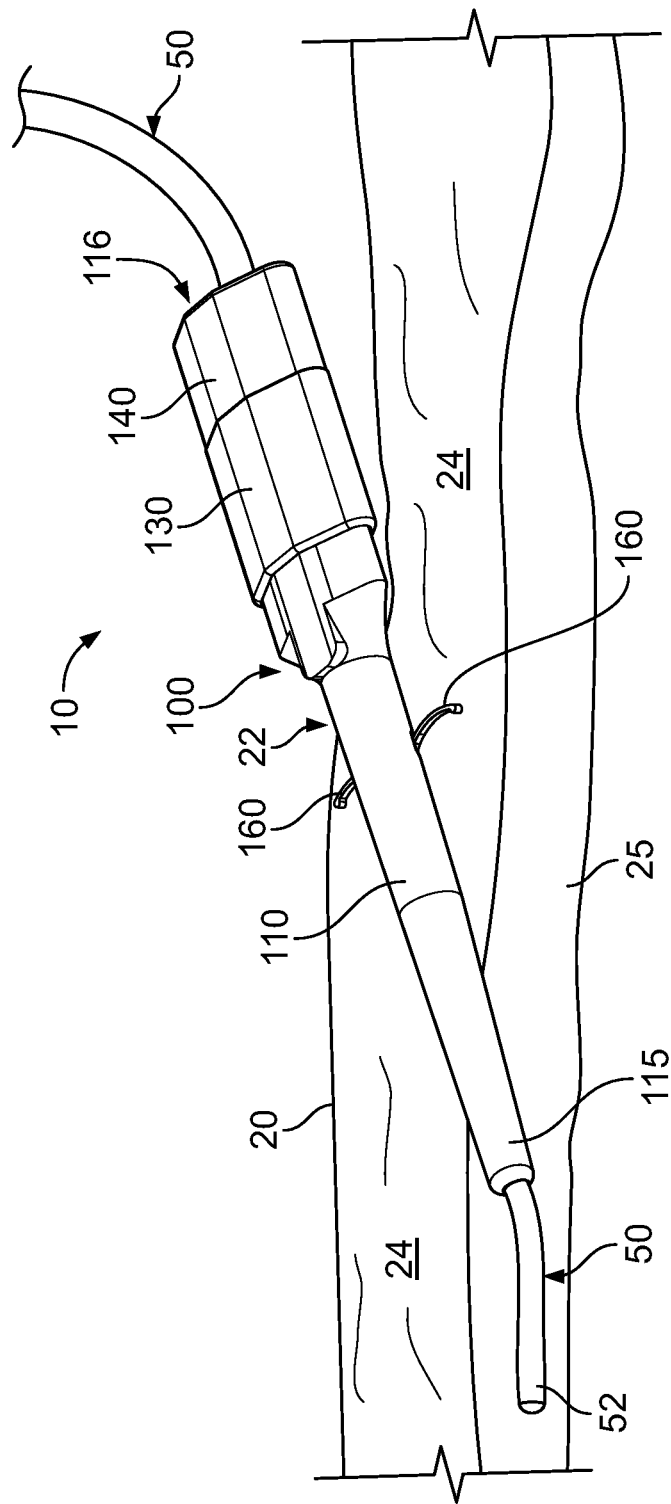
FIG. 1 is a perspective view of an anchor sleeve being advanced into a subcutaneous region and having a catheter device passing therethrough, in accordance with some embodiments.

Some embodiments of a medical device anchor system 10 include an anchor sleeve 100 and a catheter device 50 (or other medical instrument) to advance though a working channel 112 of the anchor sleeve 100. The anchor sleeve 100 may include an elongate body 110, into which the catheter device 50 can be inserted. The anchor sleeve 100 includes a distal tip portion 115 that may penetrate through a skin entry site 22 and into the subcutaneous layer 24 adjacent to the skin 20. Also, the sleeve device 100 includes a proximal portion 116 that can remain external to the skin 20 so as to provide an insertion path for the catheter device 50 or other medical instrument. The catheter device 50 is movable relative to the anchor sleeve 100, so the catheter tip 52 can be advanced through the anchor sleeve 100, into a patient's blood vessel 25 (or other body lumen), and toward a targeted body site inside the patient's body. In such circumstances, the anchor sleeve 100 can be used to retain the catheter device 50 at the skin entry site 22 on the patient's skin 20. In particular, the elongate body 110 can releasably house one or more anchors 160. As described in more detail below, the anchors 160 may comprise flexible tines that are deployable into a subcutaneous region 24 under the skin 20 so as to retain the position of the anchor sleeve 100 relative to the skin entry point 22.

In this embodiment, the anchor sleeve includes a first actuator 130 that adjusts the anchors from a non-deployed position to the deployed position depicted in FIG. 1. The first actuator 130 can be a slider mechanism that reciprocates along a portion of the elongate body 110 between a distal position and a proximal position. A user may insert the elongate body 110 through the skin insertion site 22 so that anchor deployment ports (FIG. 5) are arranged under the skin 20 the subcutaneous region 24. For example, the anchor sleeve 100 may penetrate the skin 20 through a small incision made by a physician. In some cases a dilation instrument may be used to assist in advancing the anchor sleeve 100 through the incision. After insertion, the distal tip portion 115 of the anchor sleeve 100 can be advanced into a targeted blood vessel 25 or other body lumen. When the anchor sleeve 100 is arranged in the desired position, the user can pull upon the first actuator 130 so as to slide the first actuator from a distal position to the proximal position shown in FIG. 1. As described in more detail below, the adjustment of the first actuator 130 causes the anchor tines 160 to shift from the non-deployed position to the deployed position shown in FIG. 1.

Still referring to FIG. 1, the anchor sleeve is configured to permit the catheter device 50 to be delivered through the working channel 112 either before the anchor tines 160 are deployed or after the anchor tines 160 are deployed. For example, the first actuator 130 can be shifted to cause the deployment of the anchors 160 without necessarily acting upon the catheter device 50. As such, the catheter device 50 can be advanced through the working channel 112 of the anchor sleeve 100 to deliver the catheter tip portion 52 to a targeted site inside the patient's body. When the catheter device 50 is delivered to the targeted site, the user can initiate a second actuator motion that causes the anchor sleeve 100 to releasably lock with the catheter device 50. For example, the anchor sleeve 100 may include a second actuator 140 that is at least partially rotatable relative to the elongate body 110. Thus, the user can impart a twisting motion to the second actuator 140 so as to cause the anchor sleeve 100 to retain the portion of the catheter device 50 that is arranged in the working channel 112. In some embodiments, the second actuator 140 may act upon a locking device (FIGS. 8-10) that comprises a polymeric seal member (e.g., a silicon seal). The polymeric seal member (FIGS. 8-10) can be compressed upon an outer surface of the catheter device 50 in response to the adjustment of the second actuator 140.

In these embodiments, the operation of first actuator 130 (to deploy the anchors 160) can be independent from the operation of the second actuator 140 (to cause the locking engagement between the anchor sleeve 100 and the catheter device 50). Accordingly, the anchor sleeve 100 can be equipped to isolate these two functions. For example, the first actuator 130 can be adjusted to deploy the anchor tines 160 without impeding the insertion or retraction of the catheter device 50. Also, the second actuator 140 can be operated to lock the anchor sleeve 100 in engagement with the catheter device without restricting the deployment or retraction of the anchor tines 160. Furthermore, the anchor sleeve 100 can be equipped to provide the proper amount of force for achieving each function. In some embodiments, the force required to releasably lock the anchor sleeve 100 with the catheter device 50 may be substantially greater than the force required to deploy the anchors 160 in the subcutaneous region 24. As such, the second actuator 140 can be configured to provide a mechanical advantage for the user so that the locking force is applied in a suitable manner. Also, the first actuator 130 can be configured to deploy the anchors 160 without transmitting an unnecessarily high level of force to the anchor tines 160.

Still referring to FIG. 1, the anchor sleeve 100 includes one or more subcutaneous anchors 160 for use in the temporary anchoring of at least a portion of elongate body 110 in the subcutaneous layer 24 under the skin 20. In some embodiments, the subcutaneous anchors 160 may comprise a material that exhibits superelasticity when used in the patient's body. As such, the subcutaneous anchors 160 can flexibly shift from a non-deployed position (FIG. 2) to a deployed position (FIG. 1) when in the subcutaneous layer 24. For example, the anchors 60 may be formed from a length of nitinol wire or from a sheet of nitinol material, which has been processed to exhibit superelasticity below or at about a normal human body temperature, such as below or at about 37 degrees C. The nitinol material may comprise, for example, Nickel Titanium (NiTi), Niobium Titanium (NbTi), or the like. Alternatively, the subcutaneous anchors 160 may comprise a metal material such as stainless steel, spring steel, titanium, MP35N and other cobalt alloys, or the like. In these embodiments, the subcutaneous anchors 160 can be formed from a material or materials that allow them to be adjustable from the non-deployed position to the deployed position as shown in FIG. 1.

In some embodiments, the subcutaneous anchors 160 can be flexed to a stressed condition when in the non-deployed position (e.g., prior to placement of the sleeve device 100 in a patient). For example, as described below in connection with FIG. 2, the subcutaneous anchors 160 may be retracted into an internal space of the elongate body 110 when in the non-deployed position. When deployed, as shown in FIG. 1, the subcutaneous anchors 160 can return to a shape (e.g., by exhibiting superelastic characteristics) that allows the subcutaneous anchors 160 to at least temporarily retain a portion or all of the body 110 in the subcutaneous region 24 for a period of time until the treatment with the catheter device 50 is completed.

As shown in FIG. 1, the subcutaneous anchors 160 may be designed with a curvature that facilitates the transition from the non-deployed to the deployed position. Furthermore, the curvature of the anchors 160 may be configured to eliminate or reduce the potential damage to the skin during deployment of the anchors 160. For example, the anchors 160 may include a convex curvature that abuts against the underside of the skin in a manner that prevents the tips of the anchors 160 from piercing through the underside of the skin 20. When the anchors 160 extend from the anchor deployment ports 162 (refer to FIGS. 5-7), which are positioned immediately under the skin 20 in the subcutaneous region 24, the curved shape of the anchors 160 can allow them to deploy adjacent to the skin 20 without tearing or otherwise damaging it. When deployed, the anchors 160 can serve to retain the elongate body 110 of the sleeve device 100 relative to the skin entry site 22. In some embodiments, the anchors 160 may provide a holding force of about 1 lb. or greater, depending upon the medical procedure being performed, the materials comprising the anchors 160, the geometry of the anchors 160, and/or other factors. For example, the anchors 160 may provide a holding force of about 0.5 lbs or more, about 1 lb to about 20 lbs, about 1 lb to about 5 lbs, or about 2 lbs to about 3 lbs.

In use, the subcutaneous anchors 160 can be shifted to the non-deployed position (refer, for example, to FIG. 2) prior to insertion so as to minimize resistance and possible damage to the skin 20 when inserted through the skin entry site 22. When the anchor sleeve 100 has been inserted to the intended depth inside the subcutaneous layer 24, the anchors 160 can be shifted to the deployed position (refer, for example, to FIG. 1) to provide at least temporary anchoring for the anchor sleeve 100. When removal of the anchor sleeve device 100 is desired, the subcutaneous anchors 160 can be shifted back to the non-deployed position (e.g., by adjustment of the first actuator 130) prior to removal to minimize resistance and possible damage to the skin 20 and subcutaneous region 24.

Figure 2:
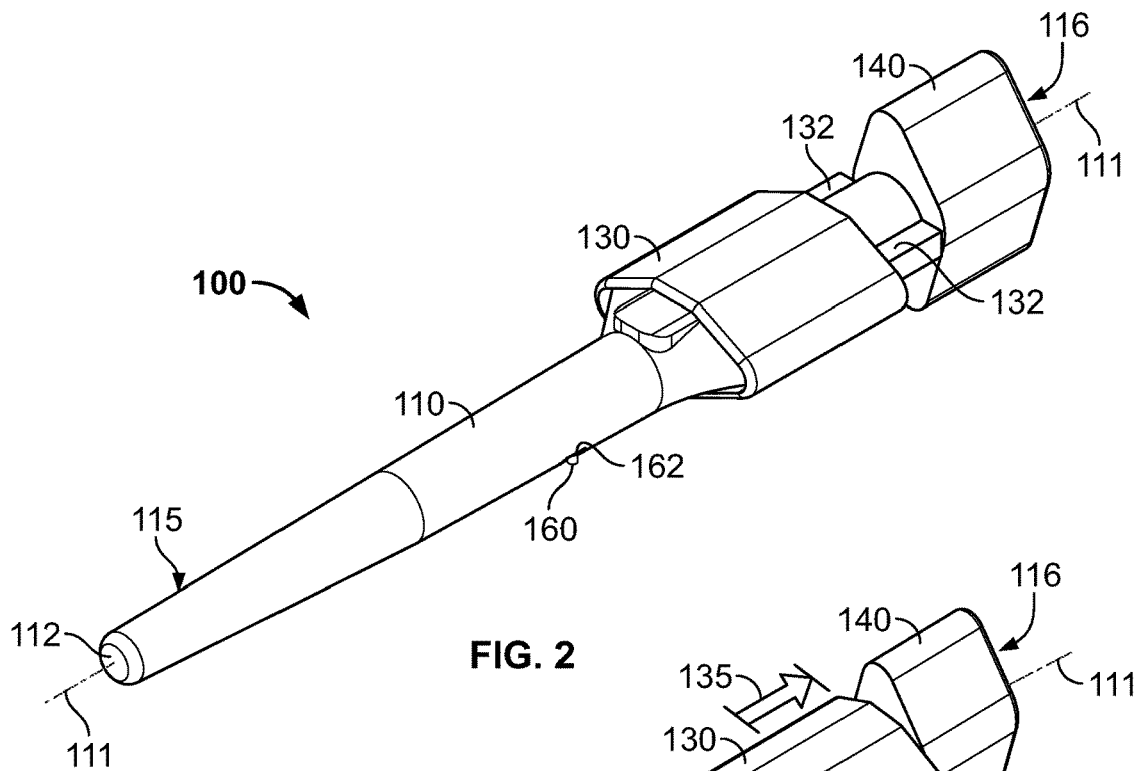
FIGS. 2-4 are perspective views of an anchor sleeve in accordance with some embodiments.
Figure 3:
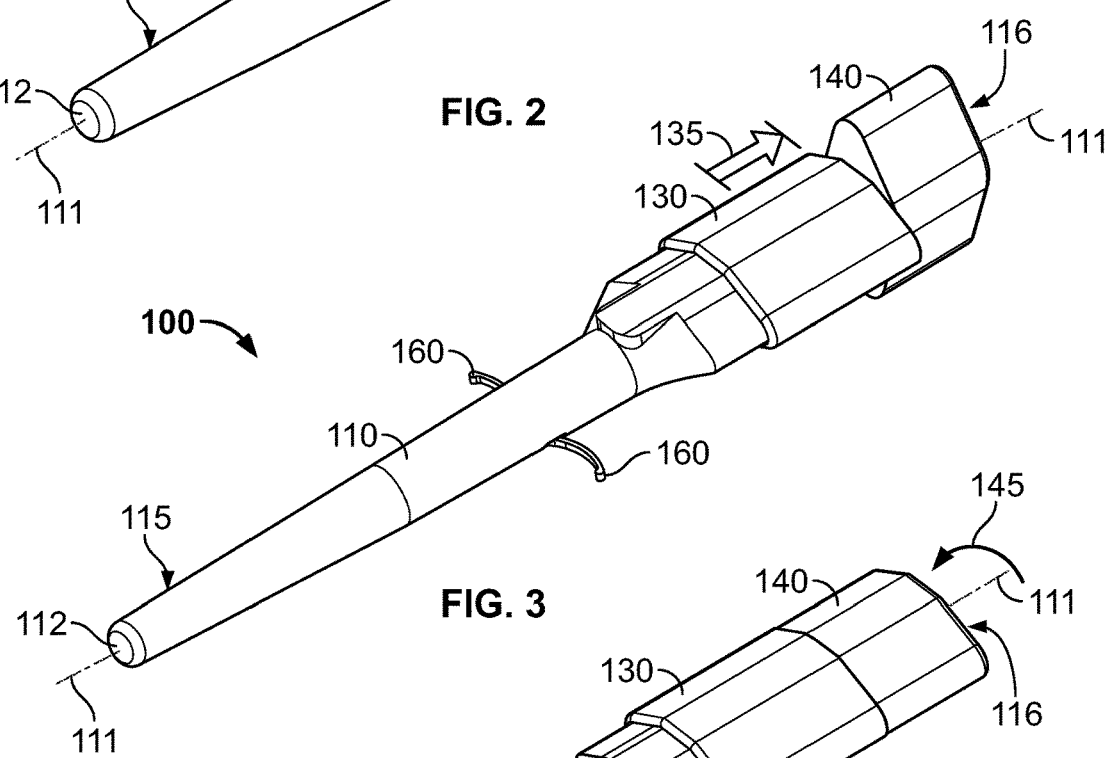
Figure 4:
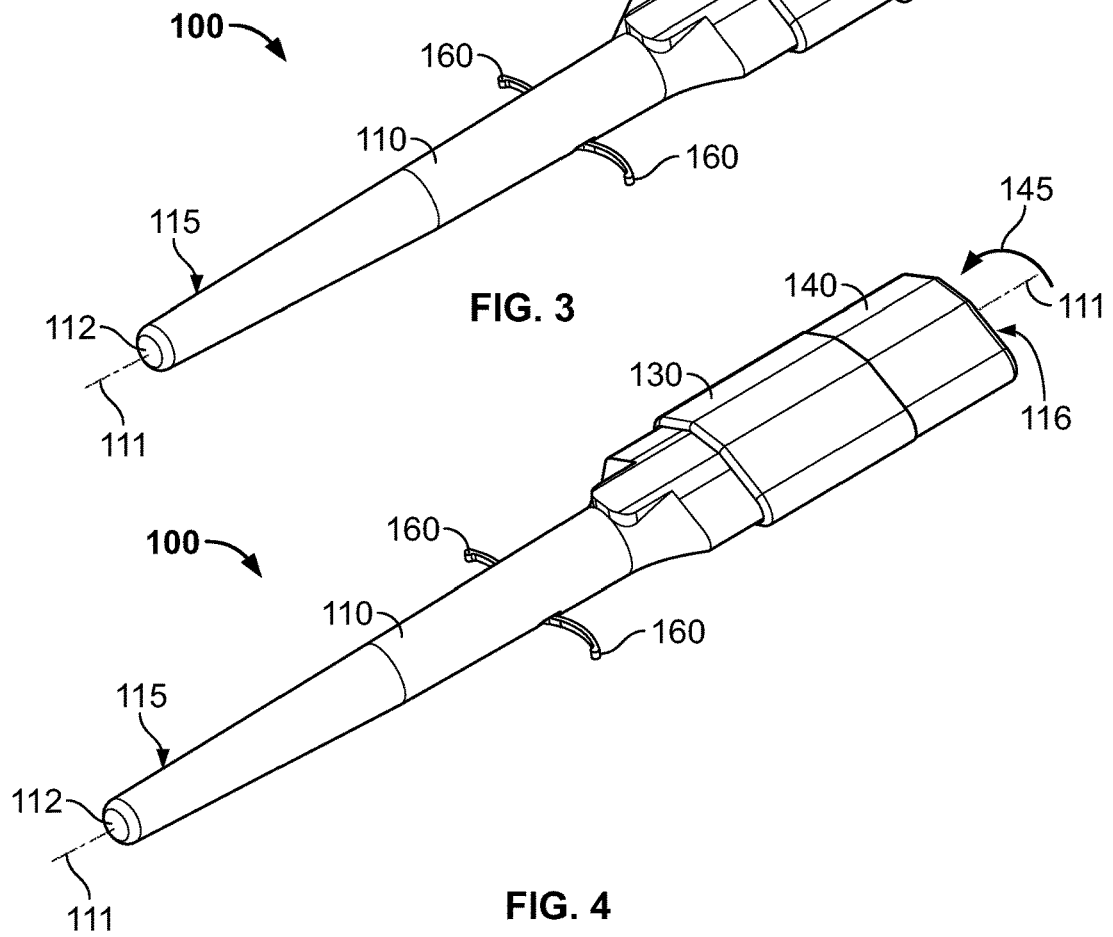

Referring now to FIGS. 2-4, some embodiments of the anchor sleeve 100 can be configured to deploy the anchors 160 in an operation that is separate from the operation of locking the anchor sleeve 100 with the catheter device 50 (not shown in FIGS. 2-4, refer to FIG. 1). As shown in FIG. 2, the anchor sleeve 100 is in a non-deployed and non-locked configuration. In particular, the anchors 160 are retained inside an internal space of the elongate body 110 in a non-deployed position. The elongate body 110 can include a number of anchor deployment ports 162 through which the anchors can be extended and retracted in response to movement of the first actuator 130. In this configuration, the first actuator 130 is arranged in a distal position (FIG. 2) before it is slidably adjusted to a proximal position (FIG. 3). Also in this configuration, the second actuator 140 is arranged in a first rotational position in which it is oriented transverse to the first actuator 130. When the anchor sleeve 100 is in the non-deployed and non-locked configuration (FIG. 2), the distal tip portion 115 can be readily inserted through the skin insertion site 22 (refer to FIG. 1) without interference from the anchors 160. Furthermore, the catheter device 50 (refer to FIG. 1) can be inserted through the working channel 112 of the anchor sleeve 100 when the anchor sleeve 100 is in the non-deployed and non-locked configuration (FIG. 2). Alternatively, the catheter device 50 can be inserted through the working channel 112 after the anchor tines 160 are deployed (described below in connection with FIG. 3). As previously described, the catheter device 50 can be advanced through the working channel 112 of the anchor sleeve 100 and into a blood vessel 25 or other body lumen for delivery to a targeted internal site.

As shown in FIG. 3, the anchor sleeve 100 can be adjusted to a deployed and non-locked configuration. In this configuration, the anchors 160 are deployed from their respective ports 162 so as to extend outwardly from the elongate body 110 of the anchor sleeve 100. In particular, the subcutaneous anchors 160 are shifted to the deployed position when the first actuator 130 is adjusted to the proximal position via the motion 135 shown in FIG. 3. The first actuator 130 can be pulled by a user to slide the actuator 130 in the proximal direction along one or more guide rails 132. The movement of the first actuator 130 transmits a deployment force to the anchor tines 160 (via an actuator rod 164 described in more detail below in connection with FIG. 9 and FIGS. 11-12) so that the anchor tines 160 at least partially extend out of the ports 162. As previously described, the anchor tines 160 can include a convexly curved shape that facilitates the transition from the non-deployed to the deployed position and reduces the likelihood of damaging the underside of the skin 20 during deployment in the subcutaneous region 24 (refer to FIG. 1). In the configuration shown in FIG. 3, the second actuator 140 is maintained in the first rotational position described above in connection with FIG. 2. As such, when the anchor tines are deployed as shown in FIG. 3, the catheter device 50 (refer to FIG. 1) can be inserted through the working channel 112 of the anchor sleeve 100 for delivery to a targeted internal site.

As shown in FIG. 4, the anchor sleeve 100 can be adjusted to a deployed and locked configuration. In this configuration, the anchors 160 are deployed to extend outwardly from the elongate body 110, and an internal locking device 150 (FIGS. 8-10) is activated to releasably retain the catheter device 50 with the anchor sleeve 100. As described in more detail below in connection with FIGS. 8-10, the internal locking device 150 can be activated when the second actuator 145 is at least partially rotated in a movement 145 about a longitudinal axis 111. In this embodiment, the second actuator 140 is shift from the first rotational position in which it is oriented transversely to the first actuator 130 to a second rotational position shown in FIG. 4. When in this second rotational position, the second actuator 140 can be oriented in alignment with the first actuator 130. For example, the second actuator 140 may undergo a rotational movement 145 of approximate 90-degrees about the longitudinal axis 111 so that the second actuator 140 generally aligns with the first actuator 130. During this rotational movement 145, the second actuator 140 can urge the internal locking device 150 (FIGS. 8-10) to act upon a portion of the catheter device 50 arranged in the working channel 112 of the anchor sleeve.

In an alternative embodiment, the second actuator 140 may include one or more structures that releasably engage the first actuator 130 when the second actuator 140 undergoes the movement 145 to align with the first actuator 130. For example, the second actuator may include connector arms (not shown in FIGS. 2-4) that mate with grooves formed in the outer surface of the first actuator 130 when second actuator 140 aligns with the first actuator 130. In such circumstances, the first actuator 130 would be locked in its proximal position (with the anchor tines 160 in the deployed position) while the second actuator 140 is in the second rotational position as shown in FIG. 4 (with the anchor sleeve 100 locked with the catheter device 50). Thus, in this embodiment, the anchor tines 160 could be retracted into the elongate body 110 only after the second actuator 140 is rotated back to the first rotational position (FIGS. 2-3), thereby unlocking the first actuator 130 from the grasp of the second actuator 140 and unlocking the catheter device 50 from the anchor sleeve 100.

Figure 5:
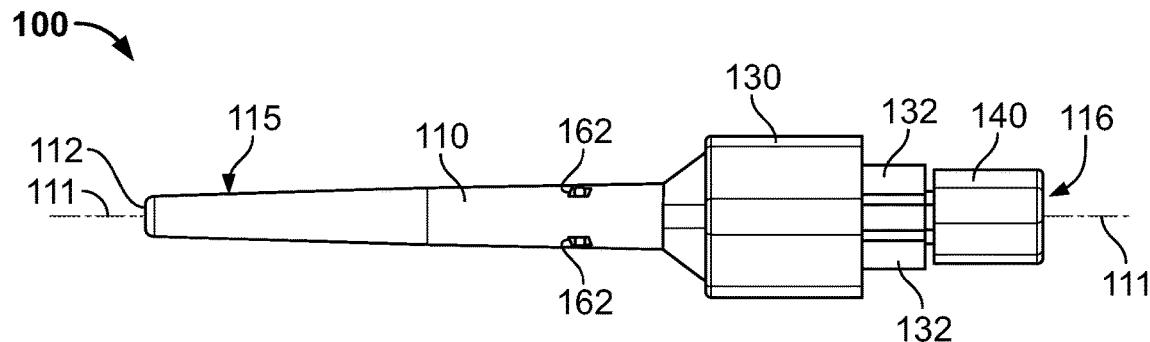
FIGS. 5-7 are bottom views of the anchor sleeve of FIGS. 2-4.
Figure 6:
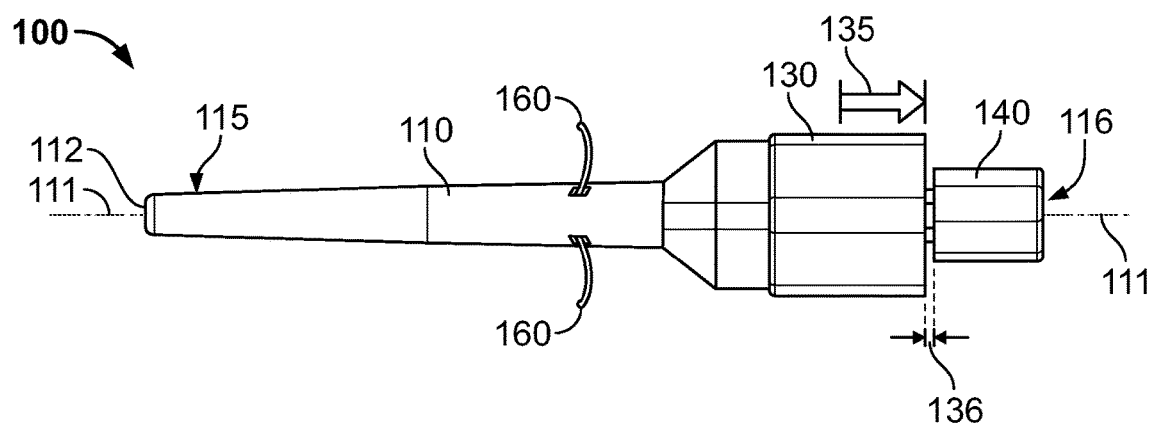
Figure 7:
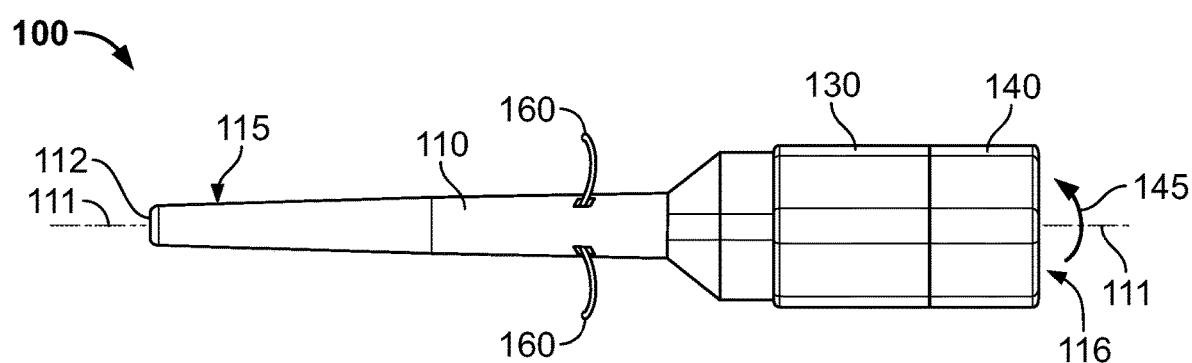

Referring now to FIGS. 5-7, the movements of the first and second actuators 130 and 140 are illustrated from a bottom view that shows the anchor deployment ports 162. As shown in FIG. 5, the anchor sleeve 100 can be arranged in the non-deployed and non-locked configuration (as previously described in connection with FIG. 2). In this configuration, the anchors 160 are retracted into an internal space of the elongate body 110 so that the anchor deployment ports 162 are viewable. The subcutaneous anchors 160 can be arranged in this non-deployed position shown in FIG. 5 prior to insertion of the anchor sleeve 100 so as to minimize resistance and possible damage to the skin 20 when the elongate body inserted through the skin entry site 22.

As shown in FIG. 6, the anchor sleeve 100 can be shifted to the deployed and non-locked configuration (as previously described in connection with FIG. 3). As such, when the anchor sleeve 100 has been inserted to the intended depth inside the subcutaneous layer 24, the anchors 160 can be shifted to the deployed position to provide at least temporary anchoring for the anchor sleeve 100. In particular, the subcutaneous anchors 160 are shifted to the deployed position when the first actuator 130 is adjusted to the proximal position via the longitudinal motion 135. The movement of the first actuator 130 transmits a deployment force to the anchor tines 160 (via an actuator rod described in more detail below in connection with FIGS. 8-10) so that the anchor tines 160 extend out of the ports 162. In this configuration shown in FIG. 6, the second actuator 140 may be spaced apart from the first actuator 130 by a gap 136. This gap 136 can be closed when the second actuator 140 undergoes is partial rotational movement 145, as described below.

As shown in FIG. 7, the anchor sleeve 100 can be adjusted to the deployed and locked configuration (as previously described in connection with FIG. 4). In this configuration, the second actuator 140 is shifted from the first rotational position (FIG. 6) to the second rotational position (FIG. 7) by the rotational movement 145 about the longitudinal axis 111. During this rotational movement 145, the second actuator 140 also closes the longitudinal gap 136 between the second actuator 140 and the first actuator 130. For example, the second actuator 140 may be in a threaded engagement with the elongate body 110 or another internal structure so that the rotational movement 145 also translates into a small longitudinal shift to at least partially close the gap 136 (FIG. 7). In some embodiments, this secondary longitudinal motion of the second actuator 140 can be used to urge the internal locking device 150 (FIGS. 8-10) to act upon a portion of the catheter device 50. Thus, the user can receive the benefit of the mechanical advantage provide by the twisting action of the second actuator 140 so as to provide a significant force the causes the locking device 150 to retain the catheter device in place. Moreover, the locking device 150 can be used to form a seal around the catheter device, as described in more detail below.

Figures 8, 9, 10:
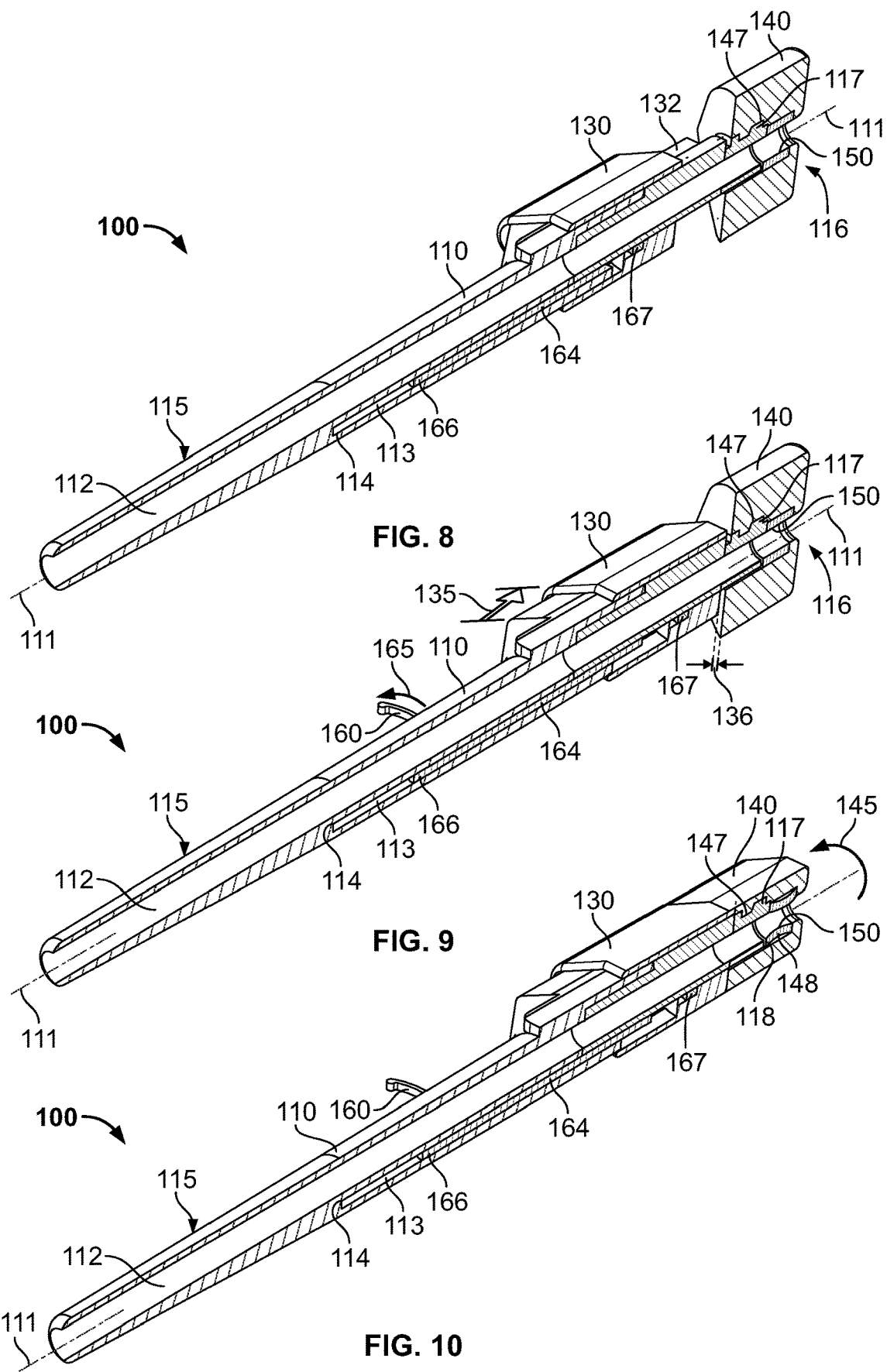
FIGS. 8-10 are cross-sectional views of the anchor sleeve of FIGS. 2-4.

Referring now to FIGS. 8-10, the adjustment of the first actuator 130 and second actuator 140 can cause a number of internal structures to move within the anchor sleeve 100. In particular, the first actuator 130 can be adjusted to cause an actuation rod 164 to move within an internal actuator channel 113. Also, the second actuator 140 can be adjusted to cause a locking device 150 to lock with a portion of the catheter device 50 arranged in the working channel 112. The operation of the locking device 150 is described in more detail below in connection with FIG. 10. It should be understood from the description herein that the catheter device 50 is removed from view in FIGS. 8-10 for purposes of illustrating the working channel 112.

As shown in FIG. 8, the anchor sleeve 100 can be arranged in the non-deployed and non-locked configuration so that the anchors 160 are retracted into an internal space of the elongate body 110 (as previously described in connection with FIG. 2). The elongate body 110 of the anchor sleeve 100 can comprise a biocompatible material, such as PEEK (polyetheretherketone), polyethylene, polyimide, or the like. The body 110 may have a modified elliptical cross-sectioned shape and may include a taper along the distal portion 115 that facilitates insertion of the anchor sleeve 100 through the skin entry site 22.

In some embodiments, the anchor sleeve 100 can include one or more internal channels 112 and 113. For example, the anchor sleeve 100 may include the working channel 112 to receive the catheter device 50 or other medical instrument, and may also include an actuator channel 113 to accommodate the actuation of the subcutaneous anchors 160. The working channel 112 can extend through the entire length of the anchor sleeve 100 from the distal tip portion 115 to the proximal portion 116. After insertion of at least a portion of the elongate body 110 into the subcutaneous region 24 (FIG. 1), the working channel 112 can be used to introduce the catheter device 50 or other medical instrument into a patient. Thus, the catheter device 50 can be introduced into the working channel 112 at the proximal portion 116 and advanced through the elongate body 110 until it emerges from the distal tip portion 115.

In the embodiment depicted in FIGS. 8-10, the anchor sleeve 100 contains a single, round working channel 112. The working channel 112 is sized to receive at least one catheter device 50 or other medical instrument. In some embodiments, the working channel 112 can have a diameter of about 3 French to about 30 French, and about 5 French to about 20 French, including particular ranges from about 3 French to about 7 French and about 12 French to about 17

French. As such, the working channel 112 can accept a wide range of catheters and medical instruments. In alternate embodiments of the anchor sleeve 100, the working channel 112 can have a different shape or size. For example, the working channel 112 may have a cross-sectional shape in the form of a square or other polygon that mates with the medical instrument to be passed therethrough. Also, the working channel 112 need not be a single lumen. In alternate embodiments, the anchor sleeve 100 may include multiple working channels, such as adjacent channels or coaxial channels that permit the introduction of multiple medical instruments (e.g., catheters, endoscopes, or the like). Furthermore, the multiple working channels may be selectively sealable so that one working channel could be accessed while another is sealed. In such cases, it would be possible to introduce and secure several catheters at different points in time.

The actuator channel 113 of the anchor sleeve 100 is formed in the elongate body 110 and can movably receive an actuator rod 164. The actuator channel 113 may be defined by one or more side walls that can slidably engage the actuator rod 164. Movement of the actuator rod 164 within the actuator channel 113 can urge the anchors 160 to extend from, or retract into, the deployment ports 162. In this embodiment, the cross-sectional shape of the actuator channel 113 and the actuator rod 164 may be quadrilateral to permit longitudinal movement of the actuator rod 164 while hindering possible rotational movement of the actuator rod 164 about its longitudinal axis.

Referring to FIG. 9, the first actuator 130 can undergo the previously described movement 135 to cause the actuator rod 164 to move within the actuator channel 113 in a longitudinal direction of the sleeve device 100. The actuator rod 164 may include a connector 167 that is coupled to the actuator 130 (described below in connection with FIGS. 11-12). As such, movement of the first actuator 130 can be translated to the actuator rod 164. The actuator rod 164 has a distal end 166 that can be advanced and retracted within the actuator channel 113 in response to the movement of the first actuator 130. The anchors 160 can be coupled to the actuator rod 164 such that movement of the actuator 130 (and the corresponding translation of the actuator rod 164 within the actuator channel 113) causes the anchors 160 to shift between the non-deployed position (FIG. 8) and the deployed position (FIG. 9).

The actuator channel 113 may not extend fully through the body 110 of the anchor sleeve 100. For example, the actuator channel 113 may extend distally to a depth that extends to a terminal end 114. In some embodiments, when the first actuator 130 is shifted to the distal position (FIG. 8), the anchor actuator rod 164 is caused to advance within the anchor actuator channel 113 such that the distal end 166 of the actuator rod 164 approaches the terminal end 114 of the actuator channel 113. In this embodiment, the anchors 160 are coupled to the actuator rod 164 so that the anchors 160 retract into the body 110 as the distal end 166 of the rod 164 approaches the terminal end 114 (shifts to the non-deployed state). In such circumstances, the anchors 160 may be flexed to a stressed condition while retained within the actuator channel 113 or other internal space of the elongate body 110.

Referring again to FIG. 9, the first actuator 130 can be pulled to generate the longitudinal movement 135, and this movement 135 is translated to the actuator rod 164 via the connector portion 167. The actuator rod 164 slides within the actuator channel 113 so that the distal end 166 of the rod 164 shifts away from the terminal end 114. This motion of the actuator rod 164 causes the tips of the anchor tines 160 to pass through the deployment ports 162 in an outward movement 165 to extend outwardly from the elongate body 110. It should be understood from the description herein that, in alternative embodiments, the actuator rod 164 and anchors 160 could be configured so that pulling the first actuator 130 to the proximal position would cause the anchors 160 to transition to their non-deployed state, while pressing the first actuator 130 into the distal position would cause the anchors 160 to transition to the deployed state.

As shown in FIG. 10, the anchor sleeve 100 can be adjusted to the deployed and locked configuration (as previously described in connection with FIG. 4). In this configuration, the second actuator 140 causes the locking device 150 to act upon a portion of the catheter device 50 so as to lock the anchor sleeve to the catheter device 50. As previously described, the catheter device 50 is removed from view in FIGS. 8-10 for purposes of illustrating the working channel 112. The second actuator 140 is shifted from the first rotational position (FIGS. 8-9) to the second rotational position (FIG. 10) by the rotational movement 145 about the longitudinal axis 111. During this rotational movement 145, the second actuator 140 also closes the longitudinal gap 136 (FIG. 9) between the second actuator 140 and the first actuator 130. In this embodiment, the second actuator 140 include an internal thread pattern 147 that mates with an external thread pattern 117 on the elongate body 110 or another internal structure. As such, the rotational movement 145 of the second actuator 140 also translates into a small longitudinal movement that closes the gap 136 (FIG. 9). This secondary longitudinal motion of the second actuator 140 can be used to urge the internal locking device 150 to act upon a portion of the catheter device 50.

Accordingly, the user an receive the benefit of the mechanical advantage from the twisting action of the second actuator 140 so as to provide a significant force the causes the locking device 150 to be compressed around an outer surface of the catheter device 50. This compression of the locking device 150 can also form a seal around the catheter device 50. For example, in some embodiments, the locking device 150 may comprise a cylindrical seal formed of a flexible material, such as silicon. As shown in FIG. 10, the cylindrical seal 150 can be arranged between an internal surface 148 of the second actuator 140 and an opposing surface 118 of the elongate body 110. Accordingly, the movement 140 of the second actuator 140 can cause the cylindrical seal to be compressed between the opposing surfaces 148 and 118. Such compression causes the cylindrical member 150 to flex inwardly (refer to FIG. 10) and engage the catheter device 50 to thereby compress around an outer surface of the catheter device 50. Thus, the locking device 150 engages the catheter device 50 to lock it in place relative to the anchor sleeve 100. Furthermore, the locking device 150 can form a seal around the outer surface of the catheter device 50 when it is compressed around the catheter device 50.

It should be understood from the description herein that the locking device 150 is not limited to the embodiments of the cylindrical polymer seal. For example, some embodiments of the locking device may include first and second jaws that operate to clamp upon the outer surface of the catheter in response to adjustment of the second actuator 140. Furthermore, in these embodiments, the locking device may include one or more seal members arranged between the opposing surfaces of the jaws. For example, a silicone seal having a half-cylinder shape can be affixed to the inner cylindrical face of the first jaw, and an opposing silicone seal having a half-cylinder shape can be affixed to the inner cylindrical face of the second jaw. As such, the opposing seal members would surround and compress the outer surface of the catheter arranged in the working channel 112.

Figure 11:
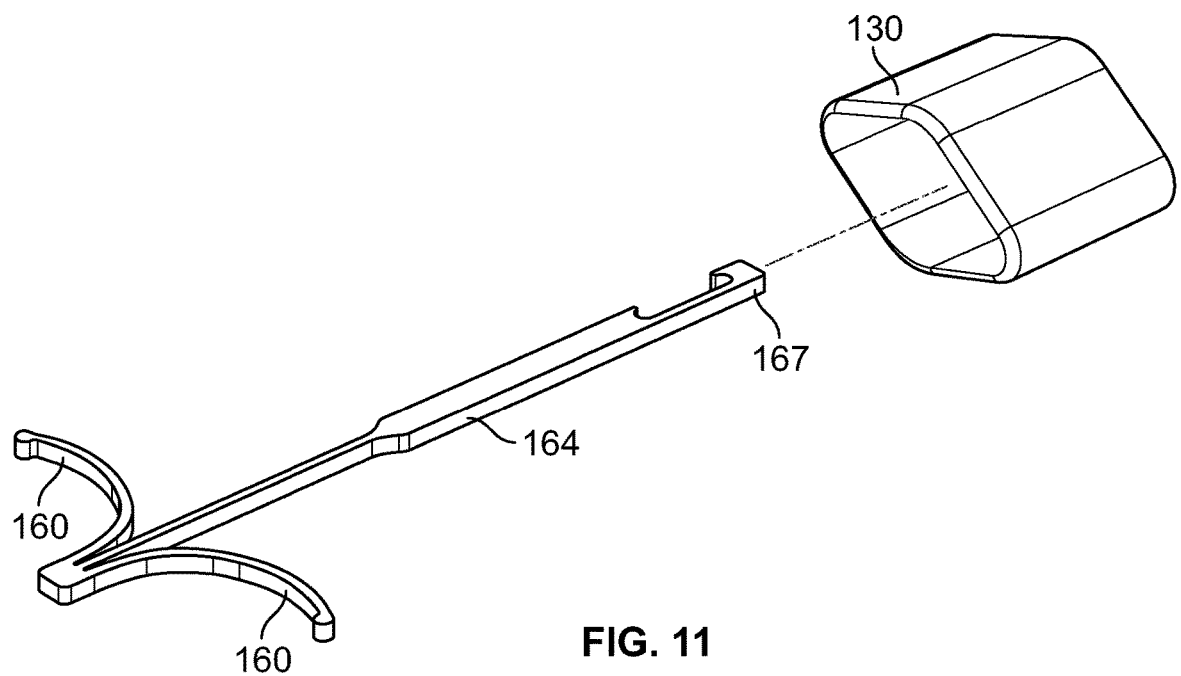
FIG. 11 is a perspective exploded view of adjustable anchor tines and a first actuator of an anchor sleeve, in accordance with some embodiments.
Figure 12:
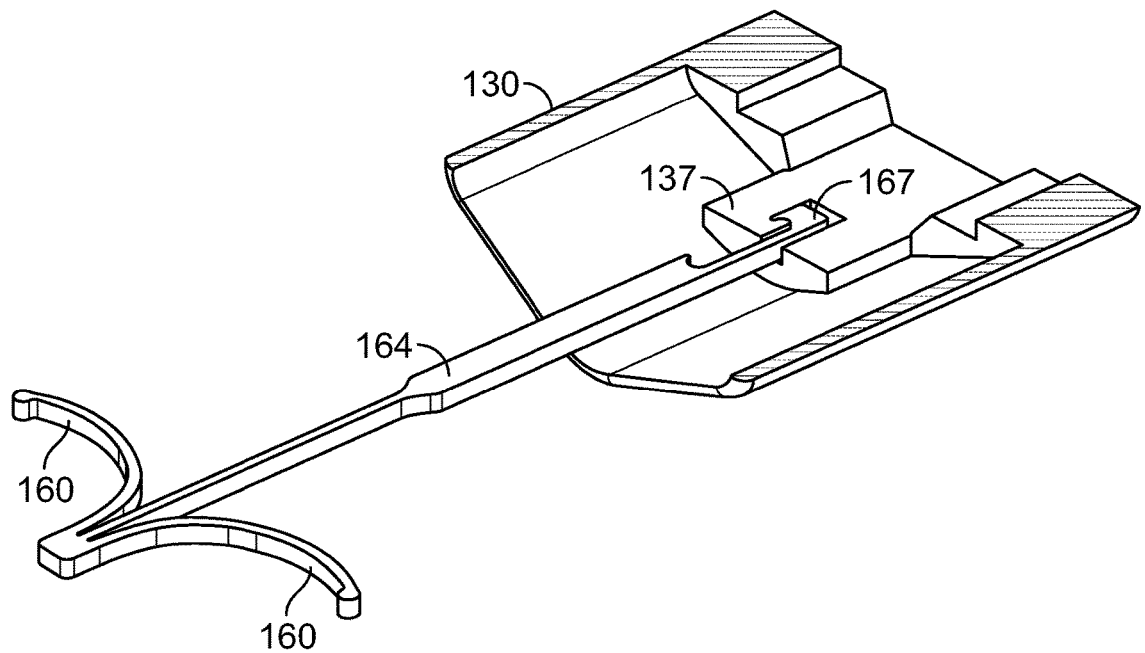
FIG. 12 is a cross-sectional view of the adjustable anchor tines and the first actuator of FIG. 11.

Referring now to FIGS. 11-12, the actuation rod 164 and the first actuator 130 can be coupled to one another so that the movement 135 (FIG. 9) of the first actuator 130 results in a corresponding movement of the actuation rod 164. In this embodiment, the actuation rod 164 includes a connector 167 that mates with a complementary connector 137 (FIG. 12) of the first actuator 130. The connection can be configured to transmit a longitudinal force from the first actuator 130 to the actuation rod 164, thereby directing the anchor tines 160 to extend from or retract into the elongate body 110 (FIGS. 8-9). As previously described in connection with FIGS. 8-9, the anchors 160 are coupled to the actuator rod 164 so that the anchors 160 retract into the elongate body 110 as the distal end 166 of the rod 164 approaches the terminal end 114 (shifts to the non-deployed state). The anchors 160 can be integrally formed with the actuator rod 164 (e.g., formed from a nitinol material or the like). It should be understood from the description herein that, in some embodiments, the anchors 160 can be joined with the actuation rod 220 at a location other than the distal end 224. For example, in other embodiments, the anchors 160 may be connected to the actuator rod 220 along a middle region of the rod 220. Also, in alternative embodiments, the anchors 160 may be non-integral with the actuator rod 220. For example, the anchors may be formed separately from the actuator rod 220 and then mounted to the rod 220 using an adhesive, a weld, a connector, or the like.

A number of embodiments of the invention have been described. Nevertheless, it will be understood that various modifications may be made without departing from the spirit and scope of the invention. Accordingly, other embodiments are within the scope of the following claims.

What is claimed is:

1. An anchor device for securing a catheter to a skin opening, comprising:
   a retainer body that defines a channel configured to engage with an exterior of a catheter;
   a first flexible anchor and a second flexible anchor movable from a non-deployed orientation to a deployed orientation in a subcutaneous region under a skin surface in which free ends of the first and second flexible anchors extend oppositely away from one another and outwardly away from a longitudinal axis of the channel of the retainer body;
   a first actuator that is movable relative to the retainer body so as to shift the first and second flexible anchors from the non-deployed orientation to the deployed orientation; and
   a second actuator that is movable, independent from the first actuator, relative to the retainer body from a first position to a second position so as to urge a lock device from a non-locked configuration in which the catheter is slidably receivable in the retainer body to a locked configuration in which the lock device is configured to inhibit slidable movement of the catheter in the channel, the second actuator having a surface in slidable engagement with the retainer body, the second actuator having at least one projection configured to engage a corresponding groove formed in the first actuator when the flexible anchors are in the deployed orientation and the lock device is in the locked configuration.

2. The anchor device of claim 1, wherein the first and second actuators are each supported by the retainer body such that operation of the first actuator is independent from operation of the second actuator.

3. The anchor device of claim 1, wherein the at least one projection of the second actuator releasably engages with the corresponding groove of the first actuator when the flexible anchors are in the deployed orientation and the lock device is in the locked configuration.

4. The anchor device of claim 1, the flexible anchors being coupled to the first actuator via a slidable internal member nonrotatably mounted in the retainer body.

5. The anchor device of claim 1, wherein the lock device has a maximum axial length that is less than a maximum axial length of the second actuator.

6. The anchor device of claim 1, wherein the lock device is housed inside an interior space of the second actuator.

7. The anchor device of claim 1, wherein the first actuator comprises a slider device that reciprocates in a direction substantially parallel to the longitudinal axis of the channel of the retainer body.

8. The anchor device of claim 7, wherein the second actuator comprises a twist device that at least partially rotates about the longitudinal axis of the channel of the retainer body, and wherein a distal end of the lock device remains generally fixed while the second actuator is adjusted to urge the lock device to compress said at least a portion of an outer surface of the catheter when the catheter is received in the channel.

9. The anchor device of claim 8, wherein the surface of the second actuator in slidable engagement with the retainer body includes a first thread pattern that mates with a second thread pattern on an external surface of the retainer body.

10. The anchor device of claim 1, wherein both the first actuator and the second actuator are positioned coaxial with the catheter when the catheter is received in the channel.

11. The anchor device of claim 1, wherein the first and second flexible anchors are retracted into an internal space of the retainer body when in the non-deployed orientation.

12. The anchor device of claim 11, wherein a wall of the retainer body through which the first and second flexible anchors are configured to extend outwardly is defined by a circular outer cross-section.

13. The anchor device of claim 1, wherein the first and second flexible anchors at least temporarily secure the retainer body in engagement with a skin insertion site when the flexible anchors are in the deployed orientation in the subcutaneous region.

14. The anchor device of claim 1, wherein the lock device comprises a polymeric member that is compressed upon the exterior of the catheter in response to adjustment of the second actuator when the catheter is received in the channel.

15. The anchor device of claim 1, wherein a gap separates the first and second actuators when the first and second flexible anchors are in the deployed orientation and the lock device is in the non-locked configuration, and the first actuator abuts the second actuator when the first and second flexible anchors are in the deployed orientation and the lock device is in the locked configuration.

16. The anchor device of claim 1, wherein a force required to urge the lock device to the locked configuration is substantially greater than a force required to deploy the first and second flexible anchors in the subcutaneous region.

17. The anchor device of claim 1, wherein the first actuator comprises a slider device that reciprocates in a direction substantially parallel to the longitudinal axis of the channel of the retainer body, and wherein the second actuator comprises a twist device that at least partially rotates about the longitudinal axis of the channel of the retainer body.

18. The anchor device of claim 17, wherein the twist device travels longitudinally along the longitudinal axis of the channel of the retainer body when the twist device at least partially rotates about the longitudinal axis of the channel of the retainer body.

19. The anchor device of claim 17, wherein a gap separates the first and second actuators when the first and second flexible anchors are in the deployed orientation and the lock device is in the non-locked configuration, and the first actuator abuts the second actuator when the first and second flexible anchors are in the deployed orientation and the lock device is in the locked configuration.

20. An anchor device for securing a catheter to a skin opening, comprising:
 a retainer body that defines a channel configured to engage with an exterior of a catheter;
 a first flexible anchor and a second flexible anchor movable from a non-deployed orientation to a deployed orientation in a subcutaneous region under a skin surface in which free ends of the first and second flexible anchors extend oppositely away from one another and outwardly away from a longitudinal axis of the channel of the retainer body;
 a first actuator that is movable relative to the retainer body so as to shift the first and second flexible anchors from the non-deployed orientation to the deployed orientation; and
 a second actuator that is movable, independent from the first actuator, relative to the retainer body from a first position to a second position so as to urge a lock device from a non-locked configuration in which the catheter is slidably receivable in the retainer body to a locked configuration in which the lock device is configured to inhibit slidable movement of the catheter in the channel, the second actuator having a surface in slidable engagement with the retainer body,
 wherein the first actuator includes an inner surface movably engaged with an outer surface of the retainer body, and the second actuator includes an outer surface that is oriented transversely to an outer surface of the first actuator when the second actuator is in the first position and that is oriented in alignment with the outer surface of the first actuator when the second actuator is in the second position.

* * * * *